United States Patent [19]

Moran et al.

[11] Patent Number: 4,627,973
[45] Date of Patent: Dec. 9, 1986

[54] SKIN MOUSSE

[75] Inventors: Robert P. Moran, Elmwood Park; Edward P. Carhart, Jr., Cliffwood Beach, both of N.J.

[73] Assignee: Charles of the Ritz Group Ltd., New York, N.Y.

[21] Appl. No.: 681,529

[22] Filed: Dec. 14, 1984

[51] Int. Cl.$^4$ ............................................. A61K 7/00
[52] U.S. Cl. .................................................... 424/47
[58] Field of Search ......................................... 424/47

[56] References Cited

FOREIGN PATENT DOCUMENTS 874627 8/1961 United Kingdom .................. 424/47

OTHER PUBLICATIONS

Sagarin, *Cosmetics Science & Technology*, "Hand Creams and Lotions", pp. 147–181 (1957).
Chem. Abst., 90: 43677b (1978).
Chem. Abst., 98: 113502g (1982).
Chem. Abst., 93: 173598z (1980).
*Drug & Cosmetic Industry*, vol. 104, No. 5, p. 146 (1969) (Kalish).
Herzka, "Lanolin Derivatives for Pressurized Formulations", pp. 331–340 (1963).

*Primary Examiner*—Albert T. Meyers
*Assistant Examiner*—F. Krosnick
*Attorney, Agent, or Firm*—Lawrence S. Levinson; Burton Rodney

[57] ABSTRACT

A skin and/or fragrance mousse or foam is provided which is in the form of a light airy stable foam which does not readily break down, and which contains a unique combination of three moisturizers, an alkoxylated methyl glucose derivative such as polypropylene glycol-20 methyl glucose ether, an alkoxylated lanolin derivative such as polyethylene glycol-85 lanolin and acetylated lanolin alcohol.

6 Claims, No Drawings

SKIN MOUSSE

FIELD OF THE INVENTION

The present invention relates to a light airy stable fragrance mousse or foam which includes a unique combination of moisturizers.

BACKGROUND OF THE INVENTION

Skin conditioners and moisturizers are usually available in the form of lotions and creams. Although many such lotions and creams are formulated to be non-greasy, in fact, practically all such skin products are inherently greasy to the touch.

Until now, hair mousses or hair foam products have been used to provide styling and body to hair. These products usually include a resinous material such as vinylmethacrylate/methacrylate copolymer to hold hair in place and to stabilize the foam. However, due to the presence of the resinous material, these hair products have a sticky consistency and therefore are messy to work with. Furthermore, use of such hair mousses often results in unsightly flaking.

DESCRIPTION OF THE INVENTION

In accordance with the present invention, there is provided a non-greasy non-sticky skin and/or fragrance product in the form of a mousse or stabilized foam. The mousse of the invention includes a unique combination of at least three moisturizers, emollients and/or emulsifiers, namely, an alkoxylated methyl glucose derivative such as polypropylene glycol-20 methyl glucose ether, an alkoxylated lanolin derivative such as polyethylene glycol-85-lanolin and acetylated lanolin alcohol, which combination provides non-greasy non-sticky moisturizing properties to the foam and stabilizes the foam so that, if desired, it maintains its structural integrity.

The mousse of the invention is formed of from about 2.1 to about 10% by weight and preferably from about 3 to about 7% by weight of the unique combination of moisturizers mentioned above, from about 15 to about 30% by weight and preferably from about 20 to about 28% by weight of alcohol, such as ethyl alcohol or isopropyl alcohol, from about 50 to about 85% by weight and preferably from about 60 to about 75% by weight water, optionally from 0 to about 5% by weight and preferably from about 0.1 to about 2% by weight of one or more auxiliary emulsifiers, emollients, humectants and/or conditioners, optionally less than about 1.5% by weight and preferably less than about 1% by weight of fragrance or perfume oil, optionally less than about 0.3% by weight color, and optionally less than about 0.5% by weight and preferably less than about 0.4% by weight of one or more preservatives, all of the about .% by weight being based on the total weight of the mousse or foam composition. The mousse of the invention when packaged will also include a hydrocarbon propellant in an amount within the range of from about 5 to about 15% by weight and preferably from about 7.5 to about 12.5% by weight of the total composition.

The unique combination of moisturizers employed herein includes, as indicated above, acetylated lanolin alcohol, an alkoxylated lanolin derivative and an alkoxylated methyl glucose derivative. Although each of these is a moisturizer, each contributes in other unexpected ways to the properties of the mousse of the invention as will be described hereinafter.

The acetylated lanolin alcohol (which is the CFTA adopted name for the reaction product of the acetylation of the lanolin alcohol fraction of refined lanolin, sold under the trademark "Acetulan" (Amerchol) or "Acetol" (Malmstrom)) will be present in an amount of within the range of from about 1 to about 5% by weight and preferably from about 1.5 to about 3.5% by weight of the total mousse formulation. The acetylated lanolin alcohol serves as an emollient-lubricant, cuts the greasing effect of other emollients that may be present, imparts a velvety after-feel to the mousse and surprisingly, and unexpectedly, enhances foam stability over prolonged periods.

The alkoxylated methyl glucose derivative employed for this emollient, humectant, fragrance enhancing and fixative properties will be present in the composition of the invention in an amount of within the range of from about 0.1 to about 3%, and preferably from about 0.1 to about 1% by weight of the total mousse composition. The alkoxylated methyl glucose derivative will preferably comprise a propoxylated methyl glucoside such as Glucam 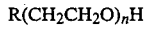P-20, trademark of Amerchol Corporation (a unit of CPC International, Inc.). Glucam P-20 is also referred to by its CTFA adopted name of PPG-20 methyl glucose ether. PPG refers to polypropylene glycol. Examples of other alkoxylated methyl glucose derivatives that may be used herein include PPG-20 methyl glucose ether or polyethylene glycol (10 or 20) ether of methyl glucose.

The alkoxylated lanolin derivative employed for its emollient and conditioner properties will be present in the composition of the invention in an amount within the range of from about 1 to about 5% and preferably from about 1.5 to about 3.5% by weight of the total mousse formulation. The alkoxylated lanolin derivatives will preferably comprise an ethoxylated polymer of lanolin such as Lanogel 61, trademark of Robinson-Wagner. Lanogel 61 is also referred to by its CFTA adopted name PEG-85 lanolin. PEG refers to polyethylene glycol and PEG-85 lanolin refers to the ethoxylated polymer of whole lanolin in which the average degree of ethoxylation is 85 moles of ethylene oxide. Examples of other alkoxylated lanolin derivatives that may be used herein include PEG-75 lanolin, PEG-40 lanolin or PEG-27 lanolin.

The proportions of each of the moisturizers forming the unique combination of moisturizers discussed above should be controlled so as to provide a weight ratio of acetylated lanolin alcohol to alkoxylated methyl glucose derivative of within the range of from about 20:1 to about 1:1 and preferably from about 15:1 to about 5:1, whereas the acetylated lanolin alcohol will be employed in a weight ratio to the alkoxylated lanolin derivative of within the range of from about 1:5 to about 5:1 and preferably from about 1:3 to about 3:1.

Other emulsifiers, emollients, humectants and/or conditioners that may be present in the mousse or foam formulation of the invention include the ethoxylated ether of coconut alcohol that conforms generally to the formula:

$$R(CH_2CH_2O)_nH$$

wherein R represents the coconut alcohol radicals referred to by the CFTA adapted name Coceth-6 (or by Promulgen D, trademark of Robinson-Wagner), a mixture of the Coceth-6 and Cetearyl alcohol (CFTA adopted name) which is a mixture of fatty alcohols comprised predominantly of cetyl and stearyl alcohols, or a polymer that conforms generally to the formula R(OCH$_2$CH$_2$)$_n$OH wherein n has an average value of 20 and R represents a blend of cetyl and stearyl radicals, referred to by the CFTA adapted name Ceteareth-20. Additional examples of auxiliary emulsifiers, emollients, humectants and/or conditioners suitable for use herein include, but are not limited to, polyethylene glycol (for example, PEG 8), sorbitol, glycerin, polyoxyethylene (26) glyceryl ether (Liponic EG1), propylene glycol, 1,3-butylene glycol or hexylene glycol, allantoin, d- or dl-panthenol, sodium 2-pyrrolidone carboxylic acid and the like.

The composition of the invention may optionally include from 0 to about 1.5% and preferably from about 0.1 to about 1% by weight of a preservative, such as imidazolidinyl urea (for example, Germall 115), methyl or propyl paraben, dimethyldimethoyl hydantoin, Dowicil 200 (Quaternium 15), that is, N-(3-chloroallyl)-hexaminium chloride, benzyl alcohol and/or phenoxyethanol, with a mixture of dimethyldimethoyl hydantoin and methyl paraben being preferred.

Preferred mousse formulations in accordance with the present invention are set out below.

| Ingredient | % by Weight |
|---|---|
| Deionized water | 60 to 80 |
| Preservatives | 0.05 to 0.4 |
| Alcohol (ethyl) | 20 to 30 |
| Acetylated lanolin alcohol | 1.5 to 3.5 |
| Alkoxylated methyl glucose derivative | 0.1 to 1 |
| Alkoxylated lanolin derivative | 1.5 to 3.5 |
| Color | 0.05 to 0.3 |
| Fragrance | 0.1 to 1 |
| Propellant | 5 to 15 |

The mousse formulation of the invention may be prepared by first mixing water-soluble ingredients such as water-soluble preservative, water-soluble auxiliary emulsifier and water while heating to 50° to 80° C. to form a solution, mixing in a separate vessel, alcohol, non-water soluble preservatives, moisturizers, emollients and fragrance oils, if any, adding this mix to the aqueous solution, cooling to room temperature, adding colors, if any, to form a concentrate, filling the concentrate into a can and adding propellant thereto.

The following Example represents a preferred embodiment of the present invention. Unless indicated to the contrary, all temperatures are expressed in degrees Centigrade.

EXAMPLE

A fragrance mousse having the following composition was prepared as described below.

| Ingredient | Concentrate (without propellant) Parts by Weight | Total Parts by Weight |
|---|---|---|
| Phase A | | |
| Deionized water | 70.6 | 63.5 |
| Methyl paraben (preservative) | 0.1 | 0.09 |
| Mixture of Cetearyl alcohol and Ceteareth-20 (75:25 mixture) (emulsifier, emollient, conditioner) | 0.3 | 0.2 |

| Ingredient | Concentrate (without propellant) Parts by Weight | Total Parts by Weight |
|---|---|---|
| Phase B | | |
| Alcohol SDA | 23 | 21 |
| Dimethyldimethoyl hydantoin | 0.1 | 0.09 |
| Polypropylene glycol-20 methyl glucose ether | 0.3 | 0.2 |
| Polyethylene glycol-85 lanolin (Lanogel-61) | 2.5 | 2.3 |
| Acetylated lanolin alcohol | 2.5 | 2.3 |
| Perfume oil | 0.6 | 0.5 |
| Phase C | | |
| Color-FD&C Blue #1, 1% aqueous solution | 0.1 | 0.09 |
| FD&C Yellow #5, 1% aqueous solution | 0.04 | 0.036 |
| Hydrocarbon Propellant (mixture of 84.56% by weight isobutane and 15.44% by weight propane) | — | 10 |

The Phase A ingredients were mixed and heated to 75° C. to form a solution.

The Phase B ingredients were mixed cold to form a mixture which was added, cold, to the Phase A solution. The so-formed mixture was cooled to 25° C. and the Phase C colors were added to form a concentrate. The concentrate (which had a specific gravity of 0.965) was filled into a can and propellant, namely about a 5.5:1 mixture of isobutane and propane was added, and an appropriate valve system employed.

The fragrance foam produced from the above concentrate was light, airy and stable and did not readily break down. When applied to the skin, it was non-greasy but velvety and soothing. It left no flaky residue while the fragrance remained on the skin for extended periods.

What is claimed is:

1. A method for enhancing stability of a moisturizer or fragrance mousse, which mousse include an effective amount of a hydrocarbon propellant, which comprises incorporating therein a mixture of acetylated lanolin alcohol, an alkoxylated methyl glucose derivative and an alkoxylated lanolin derivative, wherein said alkoxylated methyl glucose derivative is present in an amount within the range from about 0.1 to about 3% by weight of said mousse and is selected from the group consisting of polypropylene glycol-20 methyl glucose ether, polyethylene glycol-10 methyl glucose ether, and polyethylene glycol-20 methyl glucose ether, said alkoxylated lanolin derivative is present in an amount within the range of from about 1 to about 5% by weight of said mousse and is selected from the group consisting of polyethylene glycol-85 lanolin, polyethylene glycol-75 lanolin, polyethylene glycol-40 lanolin, and polyethylene glycol-27 lanolin, and said acetylated lanolin alcohol is present in an amount within the range of from about 1 to about 5% by weight of the said mousse and is the acetyl ester of lanolin alcohol.

2. The method as defined in claim 1 wherein the alkoxylated methyl glucose derivative is polypropylene glycol-20 methyl glucose ether and the alkoxylated lanolin derivative is polyethylene glycol-85 lanolin.

3. The method as defined in claim 1 wherein the hydrocarbon propellant is present in an amount within the range of from about 5 to about 15% by weight of the mousse.

4. The method as defined in claim 1 wherein the combination of alkoxylated methyl glucose derivative, alkoxylated lanolin derivative and acetylated lanolin alcohol comprises from about 2.1 to about 10% by weight of the mousse.

5. The method as defined in claim 1 wherein the alkoxylated methyl glucose derivative is present in an amount within the range of from about 0.1 to about 1% by weight of the mousse, the alkoxylated lanolin derivative is present in an amount within the range of from about 1.5 to about 3.5% by weight of the mousse and the acetylated lanolin alcohol is present in an amount within the range of from about 1.5 to about 3.5% by weight of the mousse.

6. A method for enhancing stability of a moisturizer or fragrance mousse, which mousse includes an effective amount of a hydrocarbon propellant, which comprises incorporating therein polypropylene glycol-20 methyl glucose ether in an amount within the range of from about 0.1 to about 3% by weight of the mousse, polyethylene glycol-85 lanolin in an amount within the range of from about 1 to about 5% by weight of the mousse, and the acetyl ester of lanolin alcohol in an amount within the range of from about 1 to about 5% by weight of the mousse.

* * * * *